US009510807B2

United States Patent

Tanigawa

(12) United States Patent
(10) Patent No.: US 9,510,807 B2
(45) Date of Patent: Dec. 6, 2016

(54) ULTRASOUND DIAGNOSTIC APPARATUS AND METHOD FOR DISPLAYING ELASTICITY IMAGE

(71) Applicant: GE MEDICAL SYSTEMS GLOBAL TECHNOLOGY COMPANY, LLC, Waukesha, WI (US)

(72) Inventor: Shunichiro Tanigawa, Tokyo (JP)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 134 days.

(21) Appl. No.: 14/086,730

(22) Filed: Nov. 21, 2013

(65) Prior Publication Data

US 2014/0155746 A1 Jun. 5, 2014

(30) Foreign Application Priority Data

Nov. 30, 2012 (JP) ................................ 2012-261786

(51) Int. Cl.

*A61B 8/08* (2006.01)
*A61B 8/02* (2006.01)
*A61B 8/00* (2006.01)

(52) U.S. Cl.

CPC ................ *A61B 8/485* (2013.01); *A61B 8/02* (2013.01); *A61B 8/461* (2013.01)

(58) Field of Classification Search

CPC ........... A61B 8/485; A61B 8/02; A61B 8/461
See application file for complete search history.

(56) References Cited

U.S. PATENT DOCUMENTS

2008/0071174 A1 3/2008 Waki et al.
2009/0105589 A1* 4/2009 Osaka et al. ................. 600/443
2009/0112088 A1* 4/2009 Ohuchi ............... A61B 6/5282 600/438
2009/0216123 A1 8/2009 Matsumura et al.
2011/0019894 A1 1/2011 Tanigawa
(Continued)

FOREIGN PATENT DOCUMENTS

CN 101065067 A 10/2007
CN 1011754444 A 5/2008
(Continued)

OTHER PUBLICATIONS

China 1st Office Action from corresponding Chinese application No. 201310619259.X, dated Nov. 4, 2015, 7 pages.

*Primary Examiner* — Bo J Peng

(57) ABSTRACT

An ultrasound diagnostic apparatus is provided. The ultrasound diagnostic apparatus includes a physical quantity data generating unit configured to generate physical quantity data by calculating a physical quantity related to elasticity of parts in a living tissue based on an echo signal obtained by transmission and reception of an ultrasound wave to and from the living tissue, an elasticity image data generating unit configured to generate elasticity image data including information indicative of a display form corresponding to the calculated physical quantity, and a display unit configured to display an elasticity image generated based on the elasticity image data and having a display form corresponding to the physical quantity, wherein the elasticity image is generated based on physical quantity data for a plurality of frames within a predetermined time period having a length that includes a plurality of heartbeats.

7 Claims, 13 Drawing Sheets

(56) References Cited

U.S. PATENT DOCUMENTS

| | | | | |
|---|---|---|---|---|
| 2011/0054314 | A1 | 3/2011 | Tanigawa et al. | |
| 2011/0098563 | A1 * | 4/2011 | Osaka | A61B 8/08 600/438 |
| 2011/0306884 | A1 | 12/2011 | Tanigawa et al. | |
| 2012/0016237 | A1 | 1/2012 | Tanigawa | |
| 2012/0133663 | A1 | 5/2012 | Tanigawa | |
| 2012/0203108 | A1 * | 8/2012 | Tsujita | A61B 8/08 600/445 |
| 2012/0215102 | A9 | 8/2012 | Tanigawa | |
| 2013/0030293 | A1 | 1/2013 | Tanigawa | |
| 2013/0072794 | A1 | 3/2013 | Waki | |

FOREIGN PATENT DOCUMENTS

| | | | |
|---|---|---|---|
| CN | 102327132 | A | 1/2012 |
| EP | 1800603 | A1 | 6/2007 |
| EP | 1880679 | A1 | 1/2008 |
| JP | 2007282932 | | 11/2007 |
| JP | 2008126079 | | 6/2008 |
| JP | 2008301920 | | 12/2008 |
| JP | 2012115383 | A | 6/2012 |
| WO | 2011152443 | A1 | 12/2011 |

* cited by examiner

ULTRASOUND DIAGNOSTIC APPARATUS AND METHOD FOR DISPLAYING ELASTICITY IMAGE

CROSS REFERENCE TO RELATED APPLICATIONS

This application claims the benefit of Japanese Patent Application No. 2012-261786 filed Nov. 30, 2012, which is hereby incorporated by reference in its entirety.

BACKGROUND OF THE INVENTION

The present invention relates to an ultrasound diagnostic apparatus for displaying an elasticity image expressing hardness or softness of a living tissue in a subject and a control program of the same.

An ultrasound diagnostic apparatus for synthesizing an elasticity image expressing hardness or softness of a living tissue in a subject and a B-mode image and displaying a resultant image is disclosed in, for example, Japanese Unexamined Patent Application Publication No. 2007-282932. For example, the elasticity image is generated as follows. First, a physical quantity related to elasticity of a subject is calculated on the basis of an echo signal obtained by transmitting an ultrasound wave to the subject. On the basis of the calculated physical quantity, an elasticity image made of a color according to the elasticity is generated and displayed.

The physical quantity related to elasticity is, for example, a strain. In Japanese Unexamined Patent Application Publication No. 2008-126079, a method of estimating a strain in a sound ray direction of ultrasound wave is disclosed.

In recent years, it may be desirable to evaluate a liver disease by an ultrasound diagnostic apparatus capable of displaying an elasticity image. Generation of an elasticity image by using a strain in a liver which occurs due to pulsation of the heart and blood vessels may be examined. In this case, since a strain caused by pulsation is used, a strain is not always caused, and there is also a frame having no effective strain information. To display a stable elasticity image, display of an elasticity image using data of an amount of a plurality of frames within a period in which pulsation occurs a plurality of times may be examined.

Also by elements other than pulsation such as breathing and motion of a subject (body motion), the liver is deformed and a strain occurs. However, the direction of the strain is not constant as compared with the case of pulsation. In the case of forming an image of a strain in the sound ray direction, there is a case that an elasticity image in which elasticity of a living tissue is accurately reflected cannot be obtained. To eliminate the influence of breathing and a body motion, it is desirable to conduct a test in a state where the subject holds his/her breath and does not move.

However, to obtain data of an amount of a plurality of frames in a period in which heartbeat occurs a plurality of times, time of a certain degree is necessary. There is also a case where it is difficult for the subject to hold his/her breath and stay still during the time. There is, consequently, a case that a cause of preventing acquisition of a physical amount in which elasticity of a living tissue is reflected more accurately such as breathing or body motion occurs while data of an amount of a plurality of frames is obtained, and it is difficult to acquire an elasticity image in which the elasticity of the living tissue is reflected more accurately.

BRIEF DESCRIPTION OF THE INVENTION

An ultrasound diagnostic apparatus is provided. The ultrasound diagnostic apparatus includes a physical quantity data generating unit for generating physical quantity data by calculating a physical quantity related to elasticity in each of parts in a living tissue on the basis of an echo signal obtained by transmission/reception of an ultrasound wave to/from the living tissue, an elasticity image data generating unit for generating elasticity image data having information indicative of a display form corresponding to the physical quantity calculated by the physical quantity data generating unit, and a display unit displaying an elasticity image generated on the basis of the elasticity image data and having a display form corresponding to the physical quantity. An elasticity image generated on the basis of physical quantity data of an amount of a plurality of frames within predetermined time having a length including a plurality of heartbeats is displayed in the display unit.

The predetermined time denotes length of a degree in which a plurality of heartbeats are included and length in which it is assumed that a cause preventing acquisition of a physical quantity in which elasticity of a living tissue is reflected more accurately such as breathing or body motion does not occur.

According to the systems and methods described herein, an elasticity image generated on the basis of a group of physical quantity data of an amount of a plurality of frames within the predetermined time is displayed in the display unit, so that an elasticity image in which elasticity of a living tissue is reflected more accurately can be displayed stably.

Further advantages will be apparent from the following description of exemplary embodiments as illustrated in the accompanying drawings.

DETAILED DESCRIPTION OF THE INVENTION

Hereinafter, exemplary embodiments will be described with reference to the drawings.

<First Embodiment>

Figure 1:
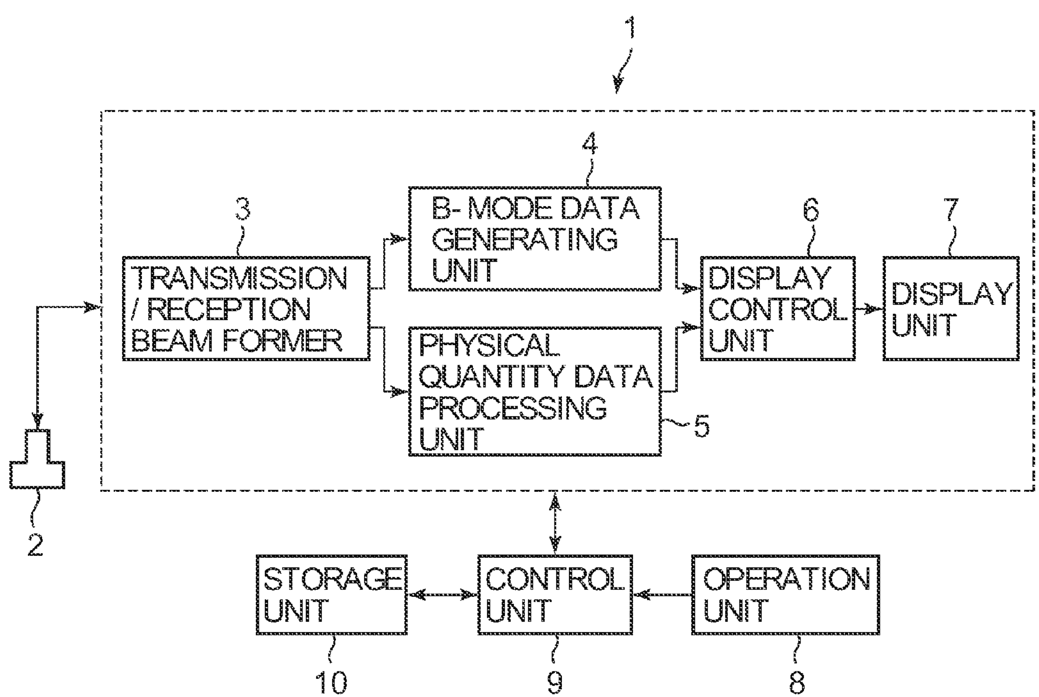
FIG. 1 is a block diagram illustrating an example of a schematic configuration of first embodiment of an ultrasound diagnostic apparatus.

First, a first embodiment will be described with reference to FIGS. 1 to 13. An ultrasound diagnostic apparatus 1 illustrated in FIG. 1 has an ultrasound probe 2, a transmission/reception beam former 3, a B-mode data generating unit 4, a physical quantity data processing unit 5, a display control unit 6, a display unit 7, an operation unit 8, a control unit 9, and a storage unit 10.

The ultrasound probe 2 transmits an ultrasound wave to a subject and receives its echo. The transmission/reception beam former 3 supplies an electric signal for transmitting an ultrasound wave from the ultrasound probe 2 under a predetermined scan condition to the ultrasound probe 2 on the basis of a control signal from the control unit 8. In such a manner, a scan with the ultrasound wave by sound ray is performed from the ultrasound probe 2. The transmission/reception beam former 3 performs signal processes such as phasing and adding process on the echo of the ultrasound wave received by the ultrasound probe 2. The echo data subjected to the signal process by the transmission/reception beam former 3 is output to the B-mode data generating unit 4 and the physical quantity data generating unit 5.

The B-mode data generating unit 4 performs B-mode processes such as a logarithmic compression process and an envelope detection process on the echo data output from the transmission/reception beam former 3 to generate B-mode data. The B-mode data may be stored in the storage unit 10.

Figure 2:
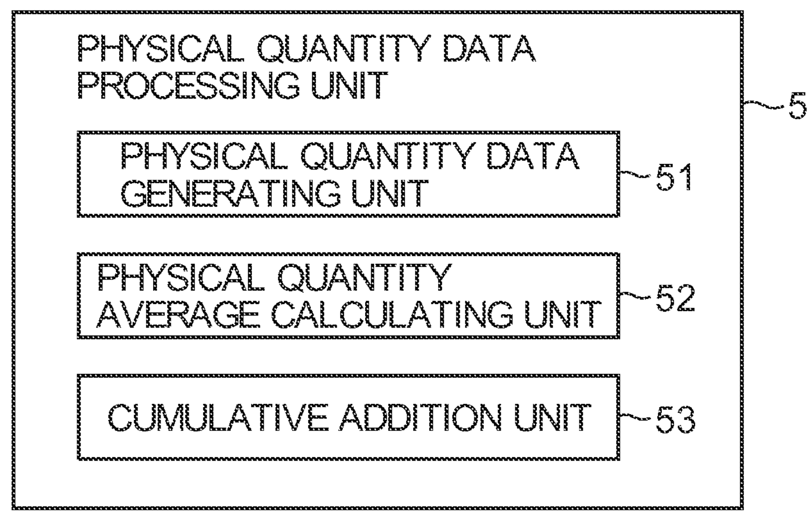
FIG. 2 is a block diagram illustrating the configuration of a physical quantity data processing unit in the ultrasound diagnostic apparatus shown in FIG. 1.

The physical quantity data processing unit 5 has, as illustrated in FIG. 2, a physical quantity data generating unit 51, a physical quantity average calculating unit 52, and a cumulative addition unit 53. The physical quantity data generating unit 51 calculates a physical quantity on elasticity of each of parts in the subject and generates physical quantity data on the basis of the echo data output from the transmission/reception beam former 3 (physical quantity calculating function). For example, as described in Japanese Unexamined Patent Application Publication No. 2008-126079, the physical quantity data generating unit 51 sets correlation windows for echo data which varies in time on the same sound ray in a scan face, performs correlating operation between the correlation windows to calculate the physical quantity on the elasticity pixel by pixel, and generates physical quantity data of one frame. Therefore, the physical quantity data of one frame is obtained from echo data of two frames and an elasticity image is generated as will be described later.

In the case where a region R of interest is set in a B-mode image as will be described later, the physical quantity data generating unit 51 may calculate the physical quantity using the inside of the region R of interest as an object.

The physical quantity data generating unit 51 calculates, as a physical quantity on the elasticity, a strain in the sound ray direction of the ultrasound wave in the example. That is, the physical quantity data is data of a strain. In the example, a strain caused by deformation of the liver due to the pulsation of the heart and blood vessels as will be described later is calculated.

The physical quantity average calculating unit 52 calculates an average value of strains by performing averaging operation in one frame from the strains obtained by the physical quantity data generating unit 51. In the case where the strain in the region R of interest is calculated, the physical quantity average calculating unit 52 calculates an average value of the strain in the region R of interest in one frame.

The cumulative addition unit 53 generates physical quantity data obtained by cumulatively adding physical quantity data of a plurality of frames. The details will be described later.

The physical quantity data may be stored in the storage unit 10.

Figure 3:
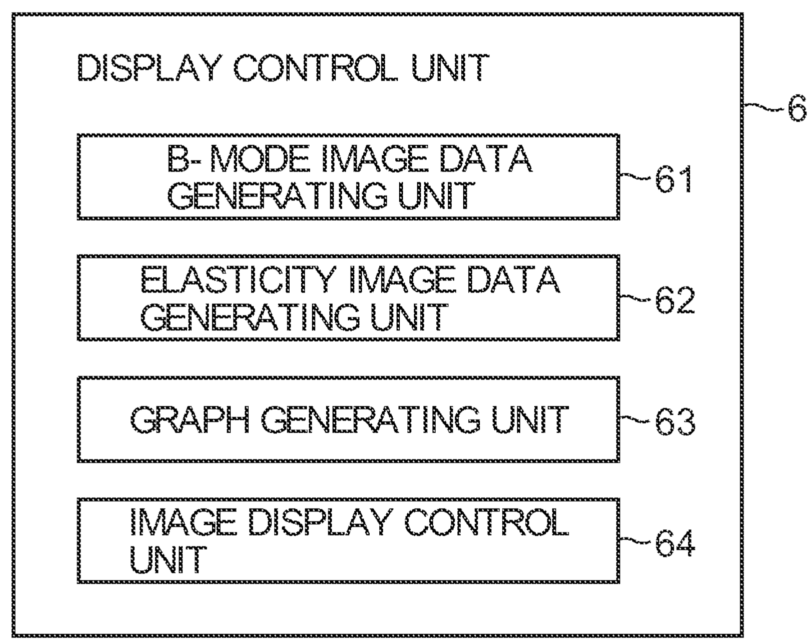
FIG. 3 is a block diagram illustrating the configuration of a display control unit in the ultrasound diagnostic apparatus shown in FIG. 1.

To the display control unit 6, B-mode data from the B-mode data generating unit 4 and physical quantity data from the physical quantity data generating unit 5 is supplied. The display control unit 6 has, as illustrated in FIG. 3, a B-mode image data generating unit 61, an elasticity image data generating unit 62, a graph generating unit 63, and an image display control unit 64.

The B-mode image data generating unit 61 performs scan conversion on the B-mode data by a scan converter to convert the data to B-mode image data having information expressing brightness according to signal intensity of an echo. The B-mode image data has information expressing, for example, brightness in 256 gray levels.

The elasticity image data generating unit 62 converts the physical quantity data to information expressing colors and performs a scan conversion by a scan converter to generate color elasticity image data having information expressing a color according to a strain (color elasticity image data generating function). The elasticity image data generating unit 62 converts the physical quantity data to gray level data, thereby generating color elasticity image data as information expressing a color assigned to the gray level. The information expressing a display mode is information expressing colors in the first embodiment.

The graph generating unit 63 generates a graph G to be displayed in the display unit 7 as will be described later.

Figure 4:
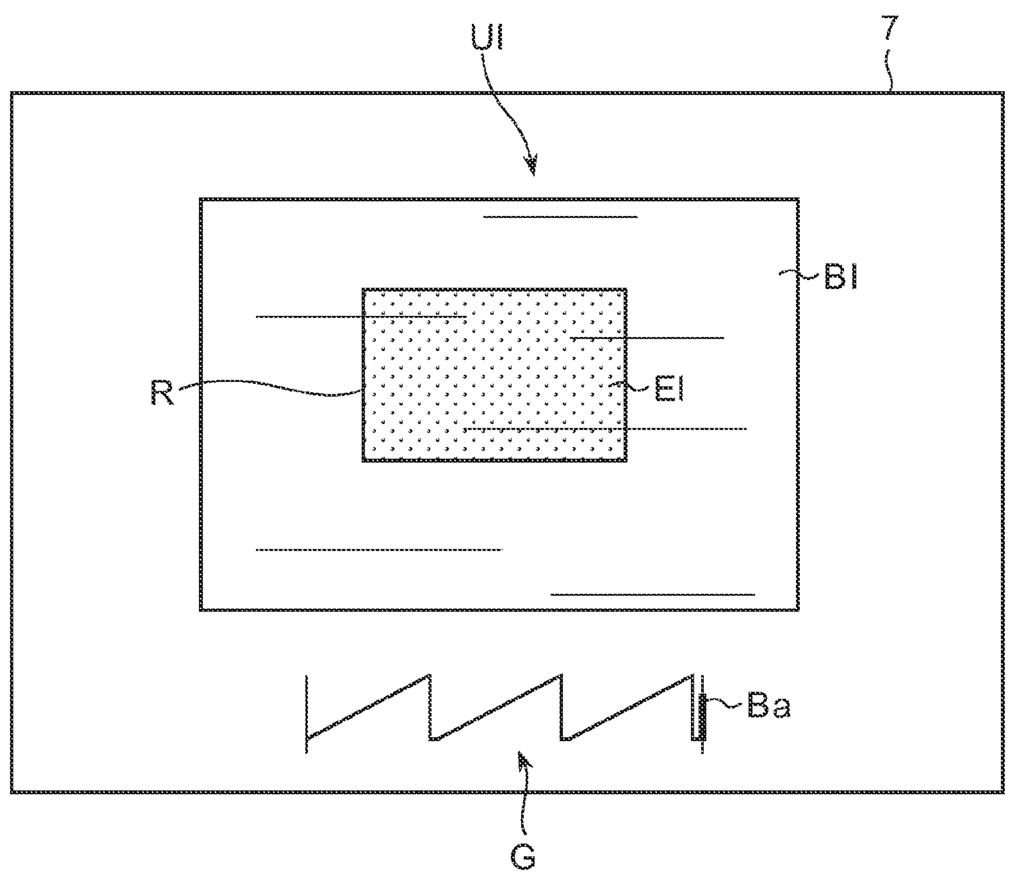
FIG. 4 is a diagram illustrating a display unit displaying a synthesized ultrasound image obtained by synthesizing a B-mode image and an elasticity image.

The image display control unit 64 synthesizes the B-mode image data and the color elasticity image data to generate image data of a synthetic ultrasound image to be displayed in the display unit 7. As illustrated in FIG. 4, the image display control unit 64 displays the image data as a synthetized ultrasound image UI obtained by synthesizing a B-mode image BI and an elasticity image EI in the display unit 7 (image display control function). The elasticity image EI is displayed in the region R of interest which is set in the B-mode image BI.

The B-mode image data and the color elasticity image data may be stored in the storage unit 10. The image data of the synthetic ultrasound image may be stored in the storage unit 10.

The image display control unit 66 displays the graph G generated by the graph generating unit 63 together with the synthetic ultrasound image UI in the display unit 7. In FIG. 4, the graph G is displayed below the synthetic ultrasound image UI. The display position of the graph G is not limited to the position illustrated in FIG. 4.

The display unit 7 includes, for example, an LCD (Liquid Crystal Display), a CRT (Cathode Ray Tube), or the like.

The operation unit 8 includes a keyboard and a pointing device (not illustrated) used by the operator to enter an instruction and information.

The control unit 9 includes a CPU (Central Processing Unit). The control unit 9 reads a control program stored in the storage unit 10 and executes the functions in the units in the ultrasound diagnostic apparatus 1 such as the physical quantity calculating function, the color elasticity image data generating function, and the image display control function.

The storage unit 10 is, for example, a semiconductor memory such as an HDD (Hard Disk Drive), a RAM (Random Access Memory), or a ROM (Read Only Memory).

The action of the ultrasound diagnostic apparatus 1 of the first embodiment will be described. The transmission/reception beam former 3 transmits an ultrasound wave from the ultrasound probe 2 to a living tissue of the subject. In the first embodiment, an ultrasound wave is transmitted to the liver of the subject by the ultrasound probe 2.

The transmission/reception beam former 3 may alternately transmit an ultrasound wave for generating a B-mode image and an ultrasound wave for generating an elasticity image. An echo signal of the ultrasound wave transmitted from the ultrasound probe 2 is received by the ultrasound probe 2.

The liver is repeatedly deformed by the pulsation of the heart and blood vessels. On the basis of an echo signal obtained from the liver which is repeatedly deformed, a synthetic ultrasound image obtained by using the deformation as a strain is generated. Specifically, when the echo signal is obtained, the B-mode data generating unit 4 generates B-mode data, and the physical quantity data generating unit 51 calculates a strain and generates physical quantity data. Further, the B-mode image data generating unit 61 generates B-mode image data on the basis of the B-mode data, and the elasticity image data generating unit 62 generates color elasticity image data on the basis of the physical quantity data. As illustrated in FIG. 4, the image display control unit 64 displays the synthetic ultrasound image UI obtained by synthetizing the B-mode image BI based on the B-mode image data and the elasticity image EI based on the color elasticity image data in the display unit 7. The elasticity image EI is displayed in the region R (indicated by dots).

In the first embodiment, on the basis of the physical quantity data obtained by cumulatively adding the physical quantity data by the cumulative addition unit 53, the color elasticity image data is generated. Hereinafter, the physical quantity data obtained by the cumulative addition will be called added physical quantity data.

Figure 5:
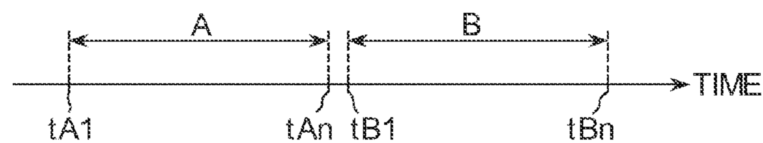
FIG. 5 is a diagram explaining cumulative addition every predetermined time.

Generation of the added physical quantity data will be described. The cumulative addition unit 53 performs cumulative addition which completes every predetermined time T, that is, cumulative addition in which the cumulative addition value is reset every predetermined time T. For example, as illustrated in FIG. 5, a period from time tA1 to time tAn is set as a period A, and a period from time tB1 to time tBn is set as a period B. Each of the period from the time tA1 to the time tAn and the period from the time tB1 to the time tBn is the predetermined time T. The cumulative addition completes in the physical quantity data of a plurality of frames in each of the periods A and B.

Figure 6:
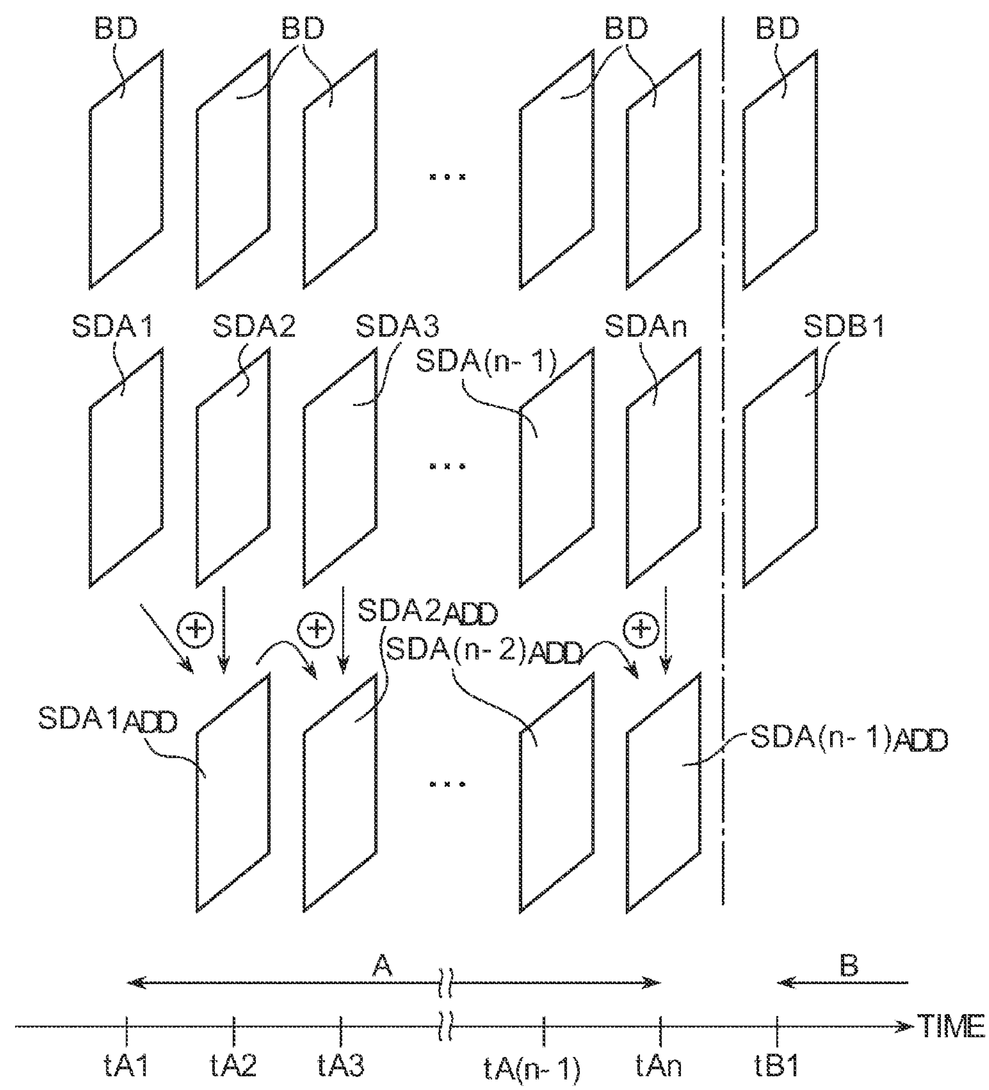
FIG. 6 is a diagram explaining addition of physical quantity data in the predetermined time illustrated in FIG. 5.
Figure 7:
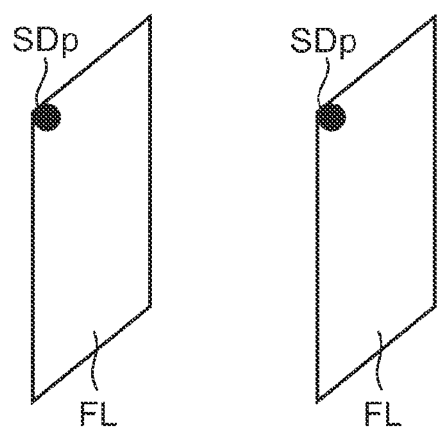
FIG. 7 is a diagram explaining addition of physical quantity data of corresponding pixels in frames.

Specifically, as illustrated in FIG. 6, the cumulative addition unit 53 adds physical quantity data SDA1 at time tA1 to physical quantity data SDA2 at time tA2 following the time tA1 to obtain added physical quantity data SDA$\mathbf{1}_{ADD}$. At the time tA2, the elasticity image EI generated on the basis of the added physical quantity data SDA$\mathbf{1}_{ADD}$ is displayed. At the time tA1, the elasticity image EI generated on the basis of the physical quantity data SDA1 at the time tA1 is displayed.

Next, the cumulative addition unit 53 adds the added physical quantity data SDA$\mathbf{1}_{ADD}$ to physical quantity data SDA3 at time tA3 to obtain added physical quantity data SDA$\mathbf{2}_{ADD}$. At the time tA3, the elasticity image EI generated on the basis of the added physical quantity data SDA$\mathbf{2}_{ADD}$ is displayed. At time after the time tA3, the cumulative addition unit 53 similarly generates added physical quantity data. At time tAn, the cumulative addition unit 53 adds added physical quantity data SDA$(n-2)_{ADD}$ obtained at time tA(n-1) to physical quantity data SDAn at the time tAn to obtain added physical quantity data SDA$(n-1)_{ADD}$. In such a manner, the cumulative addition unit 53 adds added physical quantity data obtained in an immediately preceding frame to physical quantity data in a present frame (at latest time) until time tAn to generate new added physical quantity data.

With respect to a B-mode image, an image based on B-mode data BD of each frame is displayed and updated frame by frame.

When the period B starts at time tB1, the cumulative addition unit 53 newly starts cumulative addition. That is, it does not add the added physical quantity data SDA$(n-1)_{ADD}$ obtained at the time tAn to the physical quantity data SDB1 at the time tB1. At the time tB1, the elasticity image EI based on the physical quantity data SDB1 is displayed. After the frame (not illustrated in FIG. 6) at time tB2 following the time tB1, the cumulative addition unit 53 adds the added physical quantity data obtained just before to the physical quantity data of the present frame to obtain new added physical quantity data.

Addition of physical quantity data denotes addition of physical quantity data SDp of corresponding pixels in frames FL at different times. Since the physical quantity data is raw data prior to conversion to image data, "physical quantity data according to corresponding pixels" in the above description denotes physical quantity data corresponding to corresponding pixels.

The predetermined time T denotes length including a plurality of heartbeats and is set to a degree that it is assumed a cause (hereinbelow, called "error cause") by which a physical quantity in which elasticity of a living tissue is reflected more accurately cannot be obtained such as breathing or body motion does not occur. For example, the predetermined time T is set to time corresponding to two or three heartbeats as the number of heartbeats. It is considered that, in two or three heartbeats, a period in which the error cause does not occur can be assured. The error cause is a motion of the subject other than pulsation such as breathing, a body motion, or the like. The predetermined time T may be set as a default in the storage unit 10 or the operator may set the predetermined time T by using the operation unit 8.

Figure 8:
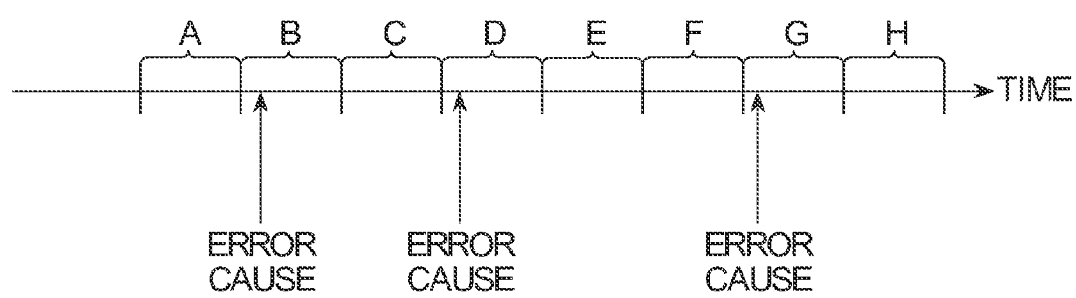
FIG. 8 is a diagram explaining predetermined time in which the cumulative addition completes.
Figure 9:
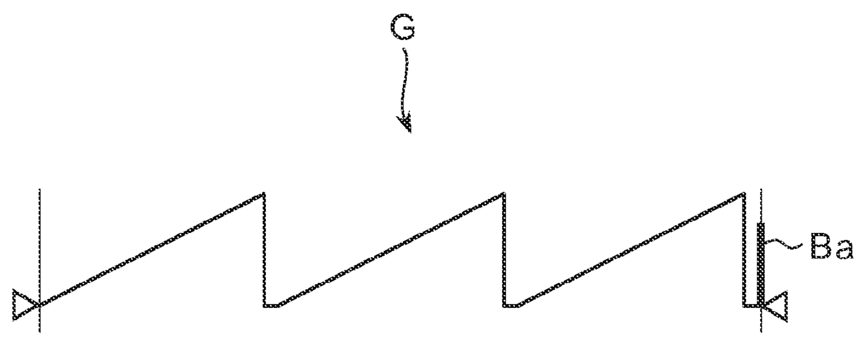
FIG. 9 is an enlarged diagram of a graph displayed in the display unit.

Specific description will be given with reference to FIG. 8. In FIG. 8, each of periods A, B, C, D, E, F, G, and H has the predetermined time T. It is assumed that an error cause occurs at positions of arrows. While the error cause occurs in the periods B, D, and G, no error cause occurs in the periods A, C, E, F, and H. Therefore, since no error cause occurs in the periods A, C, E, F, and H, an elasticity image in which elasticity of a living tissue is reflected more accurately can be obtained. Since a strain of the amount of two or three heartbeats is added, also in the period in which no heartbeat occurs, an elasticity image to which a strain caused by the heartbeats until then is added is obtained, and an elasticity image can be displayed stably.

As illustrated in FIG. 4, the image display control unit 64 displays the graph G in the display unit 7. The graph generating unit 63 generates the graph G. The graph G is a graph showing changes with time of a cumulative addition value of average values of strains. The horizontal axis denotes time, and the vertical axis denotes a cumulative addition value of average values of strains. As illustrated in an enlarged view of FIG. 9, a part of the graph G which drops vertically after a rise (increase in the cumulative addition value) is a part when the cumulative addition completes and the cumulative addition value is reset. Therefore, in the graph G, a period from the part the graph G vertically drops to a part the graph G vertically drops next expresses the predetermined time T.

An average value of strains denotes an average value of strains in the region R of interest in frames at different times. The average value of strains is calculated by the physical quantity average calculating unit 52.

In the graph G, reference characters Ba denotes a bar indicative of a frame (time) of the ultrasound image UI which is presently displayed. For example, in the case where the ultrasound image UI is displayed in a real-time manner, the bar Ba is displayed at the right end of the graph G.

Figure 10:
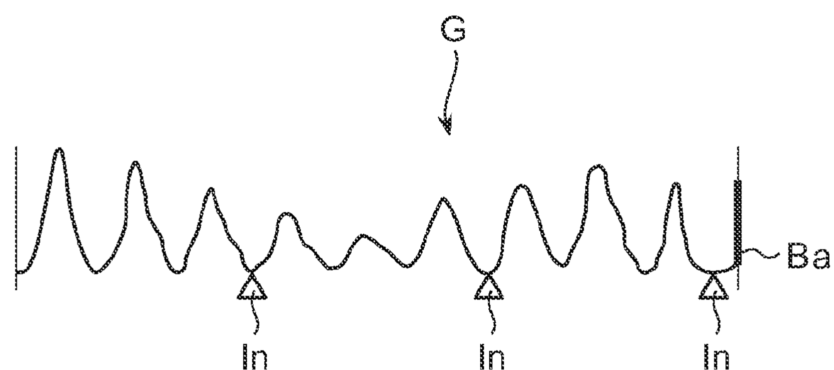
FIG. 10 is an enlarged diagram of another example of a graph displayed in the display unit.

As illustrated in FIG. 10, the graph G may be a graph expressing changes with time in the average value of strains of frames. In this case, the vertical axis denotes an average value of strains of frames. An indicator In indicative of the predetermined time T is displayed on the time axis of the graph G. The period between the indicators In adjacent to each other denotes the predetermined time T. The time axis itself is not displayed.

Figure 11:
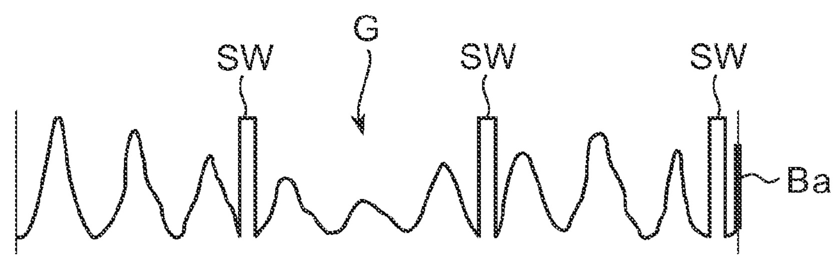
FIG. 11 is an enlarged diagram of another example of a graph displayed in the display unit.

In the case of displaying the graph G of average values of strains by frames, as illustrated in FIG. 11, a square wave SW expressing the predetermined time T may be displayed in the graph G of the average values of the strains. In this case, in the interval between the square waves SW, the waveform of the average value of strains is not displayed.

Figure 12:
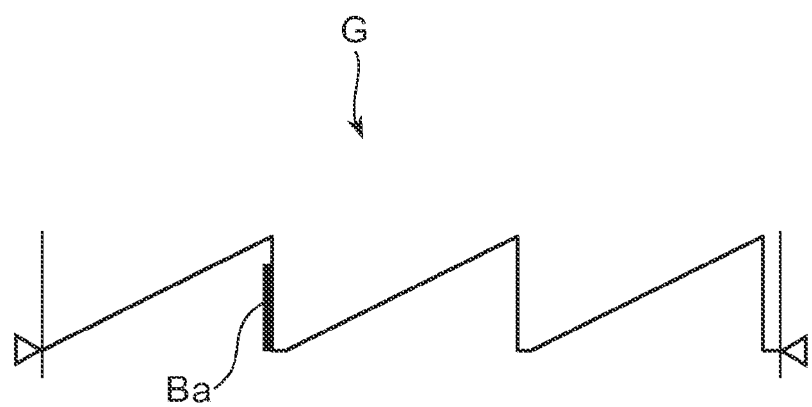
FIG. 12 is a diagram illustrating a state where a bar is moved in the graph displayed in the display unit.

In the case where the ultrasound image UI is not a real-time image but is an image based on data stored in the storage unit 10, as illustrated in FIG. 12, when the operator moves the bar Ba with the operation unit 8, the image display control unit 64 displays an image of a frame corresponding to the position of the bar Ba. For example, in the case where the bar Ba is in the position of the final frame in the period, an elasticity image based on added physical quantity data obtained by adding physical quantity data in all of frames in the period is displayed.

Figure 13:
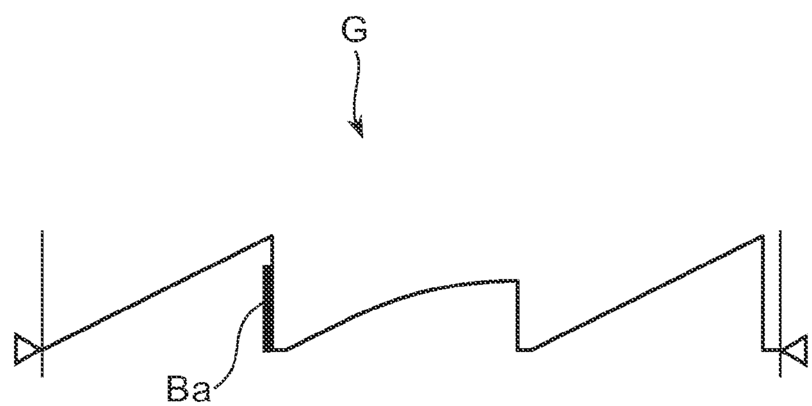
FIG. 13 is a diagram illustrating an example of movement of the bar in the graph displayed in the display unit.

Since an image of an arbitrary frame can be displayed as described above, the operator sees the graph, can move the bar Ba to a period in which no error cause occurs and the liver is properly deformed, makes an elasticity image displayed, and performs diagnosis. For example, as illustrated in FIG. 13, in a period A in the left part of the graph G, the graph G linearly increases with lapse of time. In a period B which is in the center of the graph G, the rise becomes slow. Therefore, it is considered that an echo signal capturing a deformation cannot be obtained in the period B as compared with the period A, so that the bar Ba is moved to the period A.

A modification of the first embodiment will be described. In the modification, the graph generating unit 63 generates a graph G indicating changes with time of a cumulative addition value of a quality value Q showing the degree of accurate reflection of elasticity of a living tissue in the elasticity image, and the image display control unit 64 displays the graph G in the display unit 7. The graph G is similar to that in FIG. 9.

Figure 14:
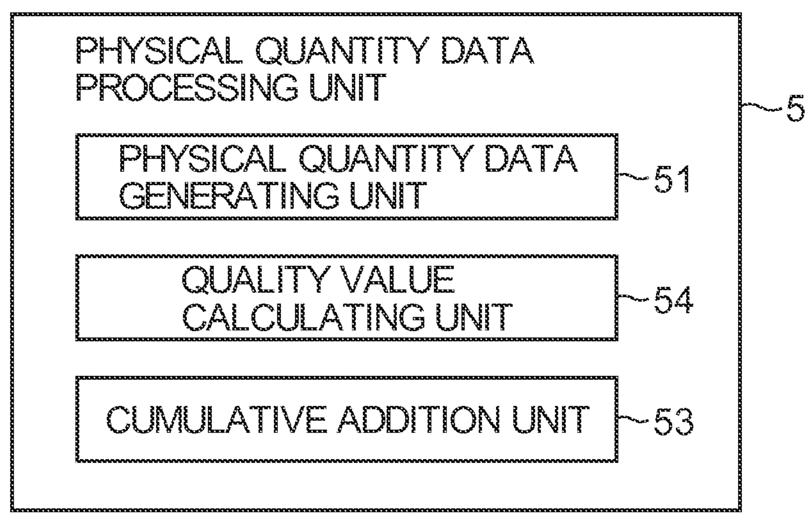
FIG. 14 is a block diagram illustrating the configuration of a physical quantity data processing unit in a modification of the first embodiment.

In the modification, as illustrated in FIG. 14, the physical quantity data processing unit 5 has a quality value calculating unit 54 in place of the physical quantity average calculating unit 52. The quality value calculating unit 54 calculates the quality value Q.

Calculation of the quality value Q by the quality value calculating unit 54 will be described. The quality value calculating unit 54 calculates an average value in the region R of interest of correlation coefficients in correlation operation by the physical quantity data generating unit 51. An average value of the correlation coefficients is the quality value Q.

In the modification, the graph generating unit 63 may generate, not the graph G of changes with time in the cumulative addition value of the quality value Q, but a graph G of changes with time in the quality value Q, and the graph G may be displayed in the display unit 7. The graph G is similar to those of FIGS. 10 and 11.

<Second Embodiment>

A second embodiment will now be described. Description of the same articles as those of the first embodiment will not be repeated.

Figure 15:
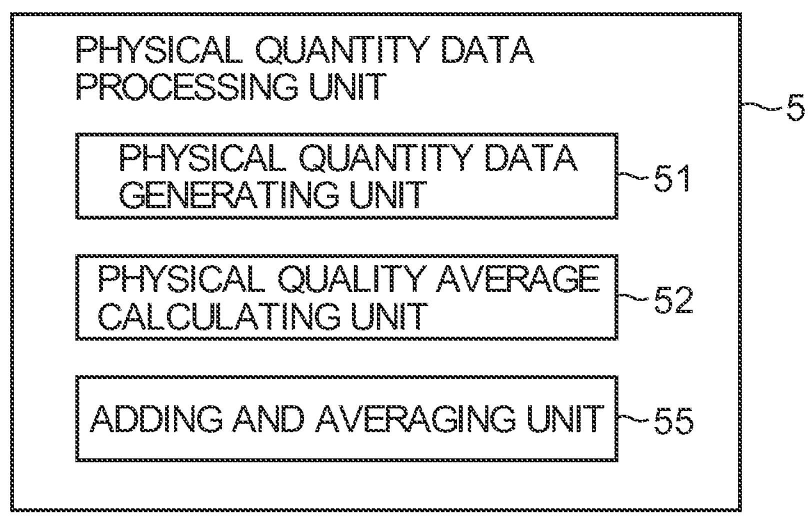
FIG. 15 is a block diagram illustrating the configuration of a physical quantity data processing unit in a second embodiment.

In the second embodiment, the physical quantity data processing unit 5 has, as illustrated in FIG. 15, the physical quantity data generating unit 51, the physical quantity average calculating unit 52, and an adding and averaging unit 55.

In the second embodiment, based on physical quantity data obtained by averaging physical quantity data by the adding and averaging unit 55, the color elasticity image data is generated, and the elasticity image EI is displayed. Hereinafter, the physical quantity data obtained by the averaging will be called average physical quantity data.

Generation of the average physical quantity data will be described. The adding and averaging unit 55 averages the physical quantity data SD of all of frames within the predetermined time T to generate average physical quantity data $SD_{AV}$. The predetermined time T is time having length similar to that in the first embodiment.

Figure 16:
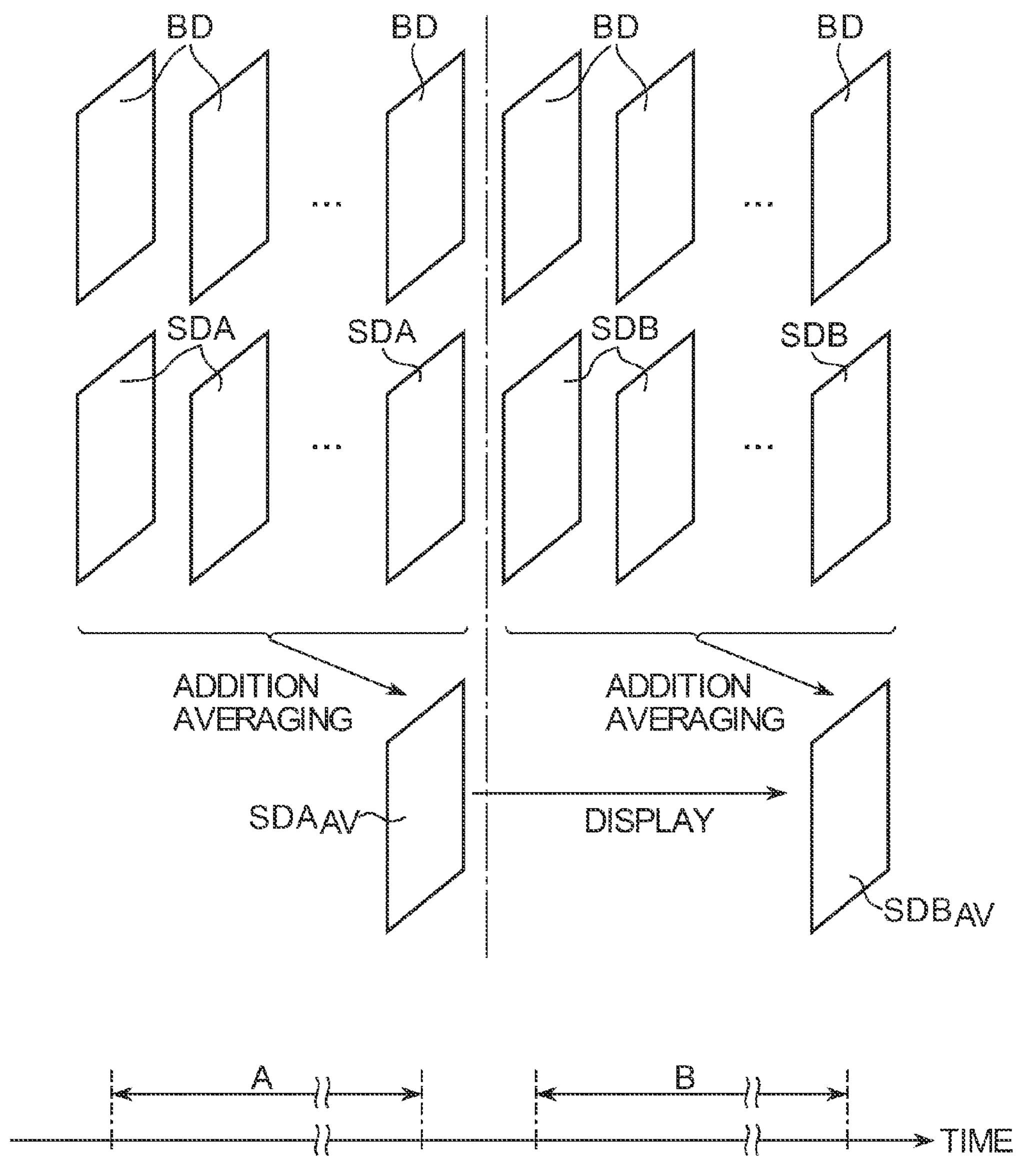
FIG. 16 is a diagram explaining averaging in the second embodiment.

For example, as illustrated in FIG. 16, the adding and averaging unit 55 averages physical quantity data SDA of all of frames within a period A having length of the predetermined time T to generate average physical quantity data $SDA_{AV}$. In the display unit 7, the elasticity image EI based on color elasticity image data generated on the basis of the average physical quantity data $SDA_{AV}$ is displayed. The elasticity image EI based on the average physical quantity data $SDA_{AV}$ is displayed until the elasticity image EI based on average physical quantity data $SDB_{AV}$ obtained by averaging physical quantity data SDB in frames in the period B subsequent to the period A is displayed. Therefore, the elasticity image is updated every predetermined time T.

With respect to a B-mode image, an image based on the B-mode data BD in each frame is displayed and updated frame by frame.

The adding and averaging unit 55 may multiply the physical quantity data of each frame with a weight coefficient to perform arithmetic operation of averaging.

Also in the second embodiment, in a manner similar to the first embodiment, the graph G (refer to FIG. 9) indicating changes with time of a cumulative addition value of average values of strains and the graph G (refer to FIGS. 10 and 11) indicating changes with time of average values of strains in different frames are displayed in the display unit 7.

Figure 17:
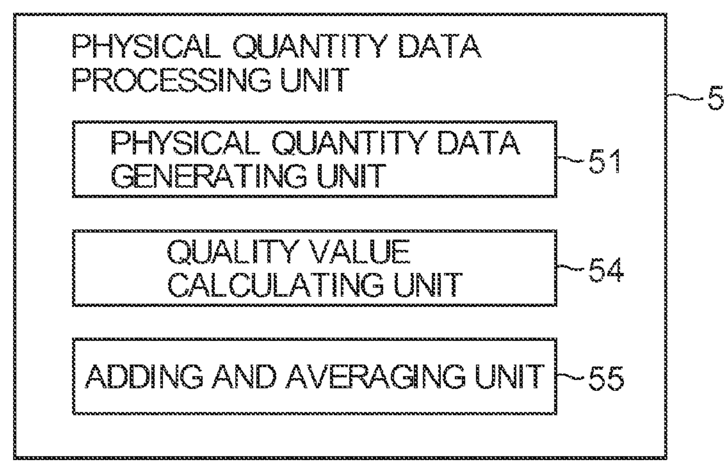
FIG. 17 is a block diagram illustrating another example of the configuration of the physical quantity data processing unit in the second embodiment.

The graph G indicating changes with time of the cumulative addition value of the quality value Q and the graph G of changes with time of the quality value Q may be also displayed in the display unit 7. In this case, as illustrated in FIG. 17, the physical quantity data processing unit 5 has the quality value calculating unit 54 in place of the physical quantity average calculating unit 52.

Also by the second embodiment described above, in a manner similar to the first embodiment, an elasticity image based on data (average physical quantity data) in a period in which no error cause occurs can be displayed, so that an elasticity image in which elasticity of a living tissue is reflected more accurately can be obtained. Since an elasticity image based on average physical quantity data obtained by averaging physical quantity data in a period of two or three heartbeats is displayed, even if there is a period where no heartbeat occurs, an elasticity image can be displayed stably.

Next, modifications of the second embodiment will be described. First, a first modification will be described. In the first modification, only physical quantity data of a frame having an average value of a strain which is equal to or larger than a predetermined threshold $S_{TH}$ is subject to averaging of the adding and averaging unit 55.

The adding and averaging unit 55 sets the threshold $S_{TH}$ of the strain every period having the length of the predetermined time T. For example, the threshold $S_{TH}$ of the strain is set, using a maximum value $S_{MAX}$ of a strain within each period as a reference, to a value smaller than the maximum value $S_{MAX}$. The maximum value $S_{MAX}$ of a strain is the maximum value of average values of strains in frames within the predetermined time T.

Concretely, the adding and averaging unit 55 adds the threshold $S_{TH}$ of a strain by the following Equation 1.

$$S_{TH}=n\times S_{MAX} \quad \text{Equation 1}$$

where n<1.

Figure 18:
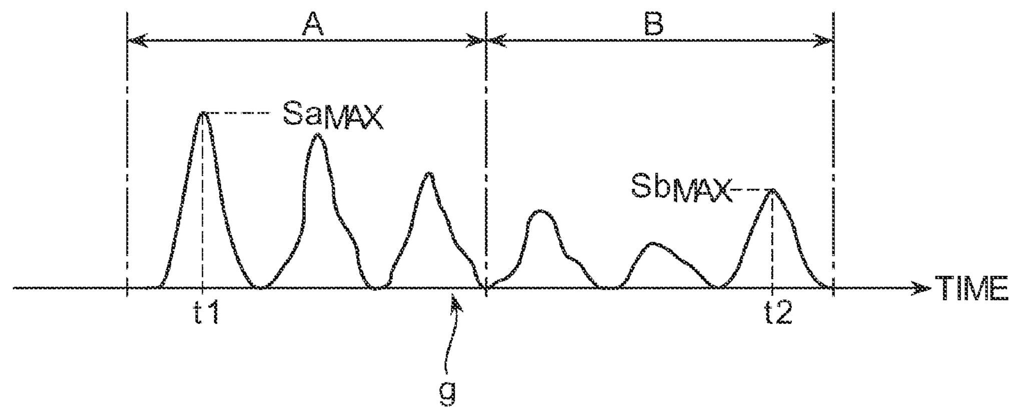
FIG. 18 is a diagram explaining setting of a threshold of a strain every period in a first modification of the second embodiment.

For example, FIG. 18 illustrates a graph "g" indicating changes with time of an average value of strains in frames. In the case where the strain at time t1 has a maximum value $Sa_{MAX}$ in a period A in the graph "g", a threshold $Sa_{TH}$ of strains in the period A is set to a value smaller than the maximum value $Sa_{MAX}$ as a reference. Specifically, the threshold $Sa_{TH}$ is calculated by the following Equation 2 obtained by substituting "$Sa_{TH}$" to "$S_{TH}$" in Equation 1 and substituting "$Sa_{MAX}$" to "$S_{MAX}$".

$$Sa_{TH}=n\times Sa_{MAX} \quad \text{Equation 2}$$

In the case where the strain at time t2 has a maximum value $Sb_{MAX}$ in the period B, a threshold $Sb_{TH}$ of strains in the period B is set to a value smaller than the maximum value $Sb_{MAX}$ as a reference. Specifically, the threshold $Sb_{TH}$ is calculated by the following Equation 3 obtained by substituting "$Sb_{TH}$" to "$S_{TH}$" in Equation 1 and substituting "$Sb_{MAX}$" to "$S_{MAX}$".

$$Sb_{TH}=n\times Sb_{MAX} \quad \text{Equation 3}$$

Figure 19:
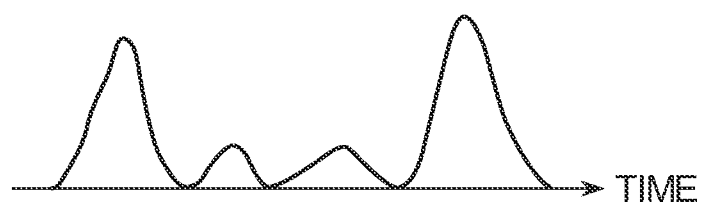
FIG. 19 is a graph illustrating changes with time in the strain.
Figure 20:
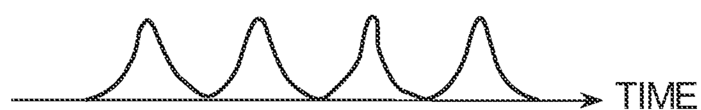
FIG. 20 is a graph illustrating changes with time in the strain.

Since $Sa_{MAX}>Sb_{MAX}$ Is satisfied, the threshold $Sa_{TH}$ of the strains in the period A becomes larger than the threshold $Sb_{TH}$ of the strains in the period B. As described above, the different thresholds of strains are set according to the maximum value $S_{MAX}$ in each period and the average physical quantity data is generated, so that proper average physical quantity data can be generated according to a strain obtained in each period. For example, in the case where the peak values of strains vary as illustrated in FIG. 19 in changes with time of strains, a threshold is set using the maximum peak value, and average physical quantity data can be generated without using data of a small peak value whose reliability is low. On the other hand, in the case where peak values of strains are stable as illustrated in FIG. 20 in changes with time of strains, the threshold according to the peak value is set. Even in the case where strains are small in an entire period, the average physical quantity data can be generated.

In the first modification of the second embodiment, at the time of setting a threshold for each period, a threshold $Q_{TH}$ of the quality value may be used in place of the threshold $S_{TH}$ of the strain. The threshold $Q_{TH}$ of the quality value is set to a value smaller than the maximum value as a reference of the quality values Q in frames in each period.

Added physical quantity data may be generated, by the cumulative addition unit 53 illustrated in FIG. 2, by cumulatively adding physical quantity data of a frame having an average value of strains equal to or larger than the threshold $S_{TH}$ of strains or physical quantity data of a frame having the threshold value $Q_{TH}$ of the quality value or larger.

Next, a second modification will be described. In the second modification, physical quantity data of a frame having a peak of a strain is subject to averaging of the adding and averaging unit 55. The peak of a strain is a part where the strain decreases after being increased.

Figure 21:
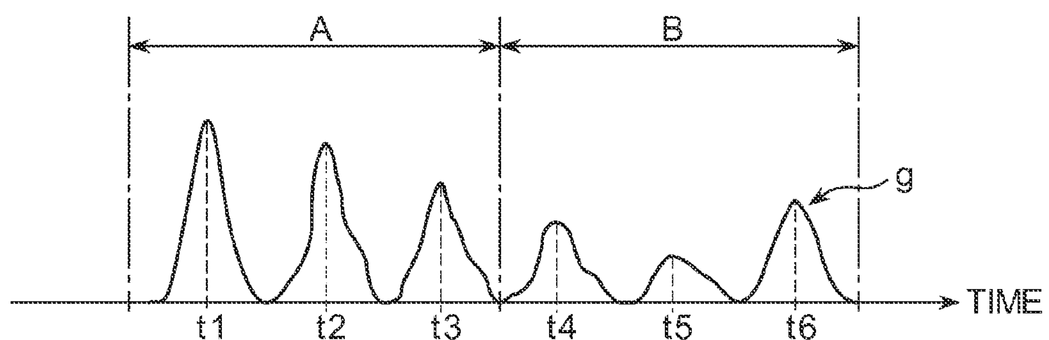
FIG. 21 is a diagram explaining averaging in a second modification of the second embodiment.

For example, FIG. 21 illustrates a graph "g" indicating changes with time of an average value of strains in one frame. In a period A, a peak of a strain occurs at times t1, t2, and t3. Therefore, in the period A, the adding and averaging unit 55 averages physical quantity data in the frame at the times t1, t2, and t3 to generate average physical quantity data. In a period B, a peak of a strain occurs at times t4, t5, and t6. Therefore, in the period B, the adding and averaging unit 55 averages physical quantity data in the frame at the times t4, t5, and t6 to generate average physical quantity data. Therefore, also in the second modification, average physical quantity data according to a strain in each period can be generated.

<Third Embodiment>

Next, a third embodiment will be described. Description of the same articles as those in the first and second embodiments will not be repeated.

In the third embodiment, the color elasticity image data is generated on the basis of physical quantity data selected from physical quantity data of a plurality of frames in the predetermined time T. Hereinafter, a specific description will be given.

Figure 22:
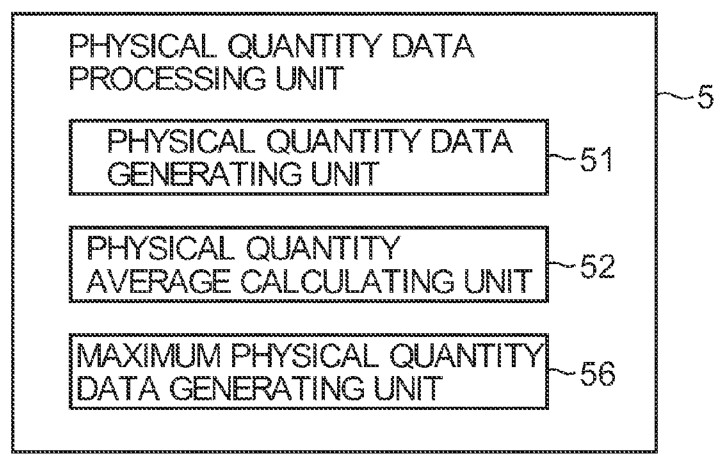
FIG. 22 is a block diagram illustrating the configuration of a physical quantity data processing unit in a third embodiment.

In the third embodiment, the physical quantity data processing unit 5 has, as illustrated in FIG. 22, the physical quantity data generating unit 51, the physical quantity average calculating unit 52, and a maximum physical quantity data generating unit 56.

The maximum physical quantity data generating unit 56 performs a strain value peak holding process to generate maximum physical quantity data made by maximum strain data in the predetermined time T. The maximum physical quantity data is physical quantity data selected from physical quantity data of a plurality of frames. The color elasticity image data is generated on the basis of the maximum physical quantity data, and the elasticity image EI is displayed.

Generation of the maximum physical quantity data will be described specifically. The maximum physical quantity data generating unit 56 compares a strain in physical quantity data in a preceding frame with that in physical quantity data in the present frame on the frame unit basis and employs the physical quantity data of a larger strain as the maximum physical quantity data. The strains are compared pixel by pixel, that is, on physical quantity data corresponding to the same pixel. It is assumed that comparison of strains completes within the predetermined time T. Therefore, when a new period starts, the maximum physical quantity data generating unit 56 sets the physical quantity data of the first frame as the maximum physical quantity data without comparing a strain in the first frame in the period and a strain in the preceding frame belonging to the preceding period.

Figure 23:
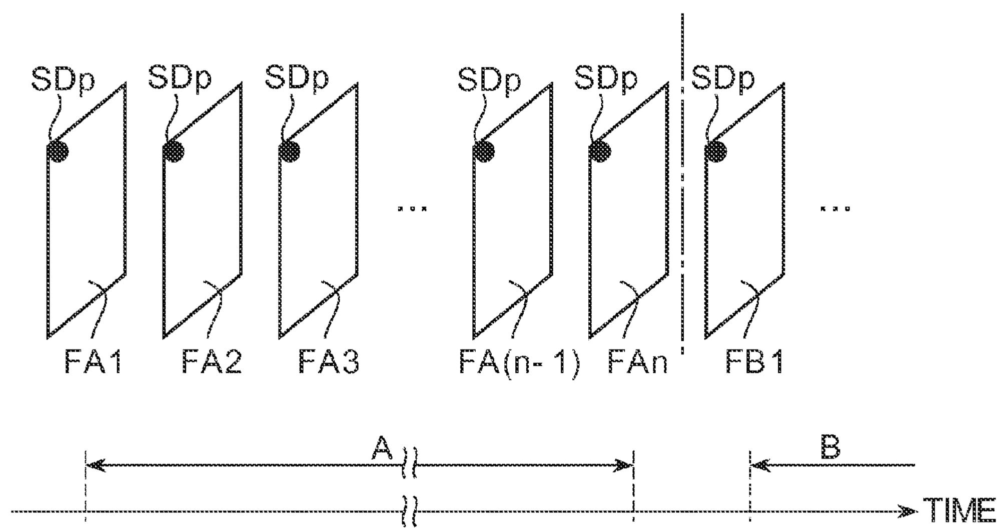
FIG. 23 is a diagram explaining generation of maximum physical quantity data in the third embodiment.

For example, as illustrated in FIG. 23, it is assumed that there is physical quantity data in frames FA1 to FAn in the period A having the length of the predetermined time. Description will be given by paying attention to physical quantity data SDp corresponding to a certain pixel in the physical quantity data in the frames FA1 to FAn. The pixel in which an image based on the physical quantity data SDp is displayed is expressed as "p" (not illustrated).

In the frame FA1 as the first frame in the period A, the physical quantity data SDp of the frame FA1 is the maximum physical quantity data, and an elasticity image EI based on the physical quantity data SDp is displayed in the pixel p.

Subsequently, in the frame FA2, the maximum physical quantity data generating unit 56 compares the physical quantity data SDp in the frame FA2 with the physical quantity data SDp in the frame FA1. The maximum physical quantity data generating unit 56 sets the larger physical quantity data SDp as the maximum physical quantity data, and an elasticity image based on the maximum physical quantity data is displayed in the pixel p.

The maximum physical quantity data generating unit 56 compares the present frame the preceding frame until the frame FAn to generate maximum physical quantity data. In such a manner, in the predetermined time T, an elasticity image based on the maximum strain physical quantity data is always displayed. For example, in the case where the value of the strain in the physical quantity data SDp in the frame FA3 is the maximum in the period A, the elasticity image EI based on the physical quantity data in the frame FA3 is continuously displayed with respect to frames after the frame FA3.

After lapse of the predetermined time T, the period A is finished, and a new period B starts. With respect to the frame FB1 as the first frame in the period B, the maximum physical quantity data generating unit 56 sets the physical quantity data SDp in the frame FB1 as the maximum physical quantity data. Also in the period B, the maximum physical quantity data generating unit 56 compares a present frame with a preceding frame to generate the maximum physical quantity data.

Also in the third embodiment, in a manner similar to the first and second embodiments, the graph G is displayed in the display unit 7.

In the third embodiment described above, in a manner similar to the first and second embodiments, an elasticity image is generated on the basis of the physical quantity data in the predetermined time T. Even there is a period in which an error cause occurs, an elasticity image in which elasticity of a living tissue is accurately reflected can be obtained in the other periods. In addition, since the elasticity image EI based on the physical quantity data of the maximum strain is continuously displayed in the predetermined time T, also in a period where there is no heartbeat, the elasticity image EI can be stably displayed.

Although the disclosure has been described above by the foregoing exemplary embodiments, obviously, the systems and methods described herein can be variously modified without departing from the spirit thereof. For example, in the third embodiment, in place of the maximum physical quantity data, physical quantity data made by an intermediate value between maximum and minimum strain values in predetermined time T which is maximum strain data in the predetermined time T may be generated.

Many widely different embodiments may be configured without departing from the spirit and the scope of the present invention. It should be understood that the present invention is not limited to the specific embodiments described in the specification, except as defined in the appended claim.

The disclosure is directed to an ultrasound diagnostic apparatus which generates an elasticity image on the basis of a group of physical quantity data of an amount of a plurality of frames within the predetermined time, and a displayed elasticity image is reflected in elasticity of a living tissue more accurately.

What is claimed is:

1. An ultrasound diagnostic apparatus comprising:

a processor configured to:

generate first physical quantity data for a first plurality of frames by calculating a physical quantity related to elasticity of parts in a living tissue based on an echo signal obtained by transmission and reception of an ultrasound wave to and from the living tissue, where the first plurality of frames is within a first predetermined time period having a length including a plurality of heartbeats;

cumulatively add the first physical quantity data for the first plurality of frames, wherein the cumulative addition is an operation completed within the first predetermined time period, where the cumulative addition results in the generation of a first cumulative addition value, and wherein the first physical quantity data as an object of the cumulative addition is data satisfying a first predetermined reference that is set based on a value of the first physical quantity data measured during one of the plurality of predetermined time periods; and generate first elasticity image data based on the first cumulative addition value, wherein the elasticity image data includes information indicative of a display form corresponding to the physical quantity;

generate second physical quantity data for a second plurality of frames by calculating the physical quantity related to elasticity of parts in a living tissue based on an echo signal obtained by transmission and reception of an ultrasound wave to and from the living tissue, where the second plurality of frames is within a second predetermined time period having a length that is the same as the first predetermined time period;

cumulatively add the second physical quantity data for the second plurality of frames, wherein the cumulative addition is an operation completed within the second predetermined time period, where the cumulative addition of the second physical quantity data results in the generation of a second cumulative addition value, and where the second cumulative addition value does not include any of the first physical quantity data, and wherein the second physical quantity data as an object of the cumulative addition of the second physical quantity data is data satisfying a second predetermined reference that is set based on a value of either the first physical quantity data or the second physical quantity data;

generate second elasticity image data based on the second cumulative addition value for the second plurality of frames, wherein the elasticity image data includes information indicative of a display form corresponding to the physical quantity;

a monitor to display the first elasticity image and the second elasticity image.

2. The ultrasound diagnostic apparatus according to claim 1, wherein the first predetermined reference is one of a reference related to the physical quantity and a reference related to a quality value indicating a degree of accurate reflection of elasticity of the living tissue in the elasticity image.

3. The ultrasound diagnostic apparatus according to claim 1, wherein the monitor further displays an image expressing the first predetermined time period.

4. The ultrasound diagnostic apparatus according to claim 1, wherein the monitor further displays at least one of a graph indicating changes over time in the first cumulative addition value of the first physical quantity and a graph indicating changes over time in the cumulative addition value of a quality value indicating a degree of accurate reflection of elasticity of the living tissue in the elasticity image.

5. The ultrasound diagnostic apparatus according to claim 1, wherein the monitor further displays at least one of a graph indicating changes over time in the physical quantity and a graph indicating changes over time in a quality value indicating a degree of accurate reflection of elasticity of the living tissue in the elasticity image.

6. A method for displaying an elasticity image, the method comprising:

generating physical quantity data for a plurality of frames by calculating a physical quantity related to elasticity of parts in a living tissue based on an echo signal obtained by transmission and reception of an ultrasound wave to and from the living tissue;

cumulatively adding the physical quantity data for the plurality of frames within a predetermined time period having a length including a plurality of heartbeats, wherein the cumulative addition is an operation completed within any of a plurality of predetermined time periods, wherein each of the plurality of predetermined time periods has a length including a plurality of heartbeats, and wherein the physical quantity data as an object of the cumulative addition is data satisfying a predetermined reference that is set based on a value of the physical quantity data measured during at least one of the plurality of predetermined time periods; and generating elasticity image data based on the added physical quantity data, wherein the elasticity image data includes information indicative of a display form corresponding to the physical quantity;

generating an elasticity image based on the elasticity image data; and displaying the elasticity image generated based on the elasticity image data and having a display form corresponding to the physical quantity, wherein the elasticity image is an image obtained by adding and averaging the physical quantity data for the plurality of frames within the predetermined time period, wherein the physical quantity data is data satisfying a predetermined reference that is set each of predetermined time periods.

7. A method for displaying an elasticity image, the method comprising:

generating first physical quantity data for a first plurality of frames by calculating a physical quantity related to elasticity of parts in a living tissue based on an echo signal obtained by transmission and reception of an ultrasound wave to and from the living tissue, where the first plurality of frames is within a first predetermined time period having a length including a plurality of heartbeats;

cumulatively adding the first physical quantity data for the first plurality of frames, where said cumulatively adding is completed within the first predetermined time period, where the cumulative addition results in the generation of a first cumulative addition value, where the cumulatively added first physical quantity data satisfies a first threshold set based on a value of the first physical quantity data measured during the first predetermined time period;

generating first elasticity image data based on the cumulatively added first physical quantity data for the first plurality of frames, where the elasticity image data includes information indicative of a display form corresponding to the physical quantity;

generating second physical quantity data for a second plurality of frames by calculating a physical quantity related to elasticity of parts in a living tissue based on an echo signal obtained by transmission and reception of an ultrasound wave to and from the living tissue, where the second plurality of frames is within a second predetermined time period having a length including a plurality of heartbeats, and where the second predetermined time period is the same length as the first predetermined time period;

cumulatively adding the second physical quantity data for the second plurality of frames, where said cumulatively adding is completed within the second predetermined time period, where the cumulative addition results in the generation of a second cumulative addition value, where the cumulatively added second physical quantity data satisfies a second threshold set based on a value of the second physical quantity data measured during the second predetermined time period;

generating elasticity image data based on the cumulatively added second physical quantity data for the second plurality of frames, where the elasticity image data includes information indicative of a display form corresponding to the physical quantity;

generating a first elasticity image based on the first elastic image data;

generating a second elasticity image based on the second elastic image data;

displaying the first elasticity image on a monitor; and displaying the second elasticity image on the monitor.

* * * * *